United States Patent [19]

Wysham

[11] Patent Number: 4,957,117
[45] Date of Patent: Sep. 18, 1990

[54] ONE-HANDED PERCUTANEOUS TRANSLUMINAL ANGIOPLASTY STEERING DEVICE AND METHOD

[75] Inventor: Douglas G. Wysham, Shoreview, Minn.

[73] Assignee: Ramsey Foundation, St. Paul, Minn.

[21] Appl. No.: 266,584

[22] Filed: Nov. 3, 1988

[51] Int. Cl.$^5$ ............................................. A61B 5/00
[52] U.S. Cl. ........................................ 604/95; 604/95
[58] Field of Search ................ 604/95, 164, 170, 330, 604/159; 128/656-658, 772, 303; 226/127

[56] References Cited

U.S. PATENT DOCUMENTS

| | | |
|---|---|---|
| 3,698,396 | 10/1972 | Katerndahl et al. |
| 3,913,584 | 10/1975 | Walchle et al. |
| 4,411,653 | 10/1983 | Razi |
| 4,411,655 | 10/1983 | Schreck |
| 4,417,886 | 11/1983 | Frankhouser et al. |
| 4,533,960 | 11/1985 | Lazarus et al. |
| 4,540,404 | 9/1985 | Wolvek |
| 4,559,041 | 12/1985 | Razi |
| 4,615,472 | 10/1986 | Nash ................................ 604/159 |
| 4,619,274 | 10/1986 | Morrison |
| 4,726,369 | 2/1988 | Mar |
| 4,799,496 | 1/1989 | Hargreaves et al. ................. 604/95 |

OTHER PUBLICATIONS

The ACS ® Accessories brochure, ©1986 Advanced Cardiovascular Systems, Inc., Mountain View, Calif.
The ACS ® Product catalog, ©1984 Advanced Cardiovascular Systems, Inc., Mountain View, Calif.
The ACS ® leaflet, published prior to Nov. 3, 1988, Advanced Cardiovascular Systems, Inc., Mountain View, Calif.
The USCI ® Probe TM brochure, ©1987 C. R. Bard, Inc., Billerica, Mass.
The USCI ® Steering Handle Directions for Use, published prior to Nov. 3, 1988, C. R. Bard, Inc., Billerica, Mass.

Primary Examiner—Stephen C. Pellegrino
Attorney, Agent, or Firm—Merchant, Gould, Smith, Edell, Welter & Schmidt

[57] ABSTRACT

A steering device for directing passage of a remote portion of a length of wire, preferably a guide wire for use in percutaneous transluminal angioplasty. The steering device includes a releasable gripping mechanism for releasably gripping a proximate portion of the length of wire. The gripping mechanism includes and opposing gripping surfaces which cooperate to grip the proximate portion of the length of wire therebetween when said gripping mechanism is manipulated by the exertion of a translational force so that it is in a gripping position and the device grips the length of wire.

22 Claims, 4 Drawing Sheets

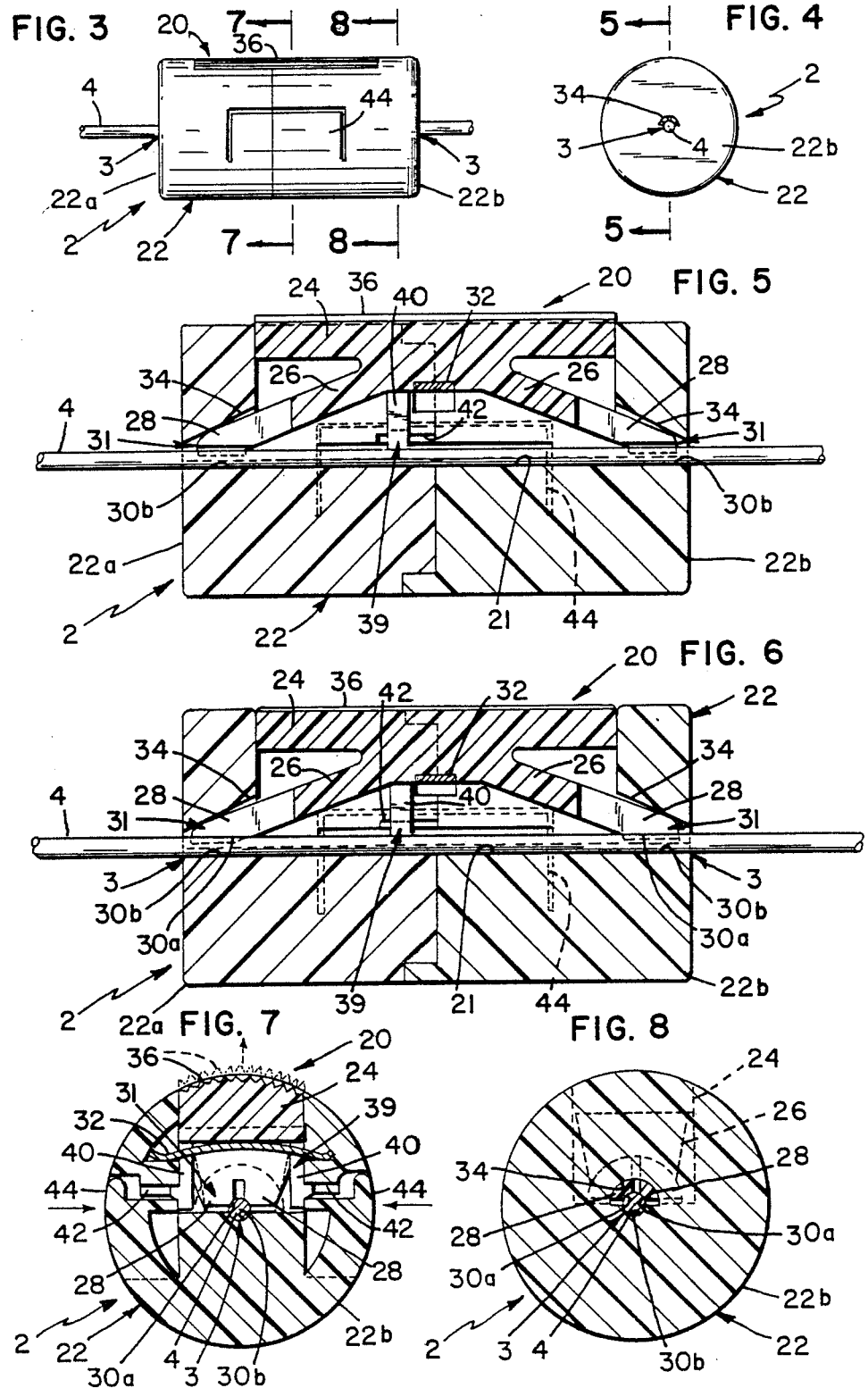

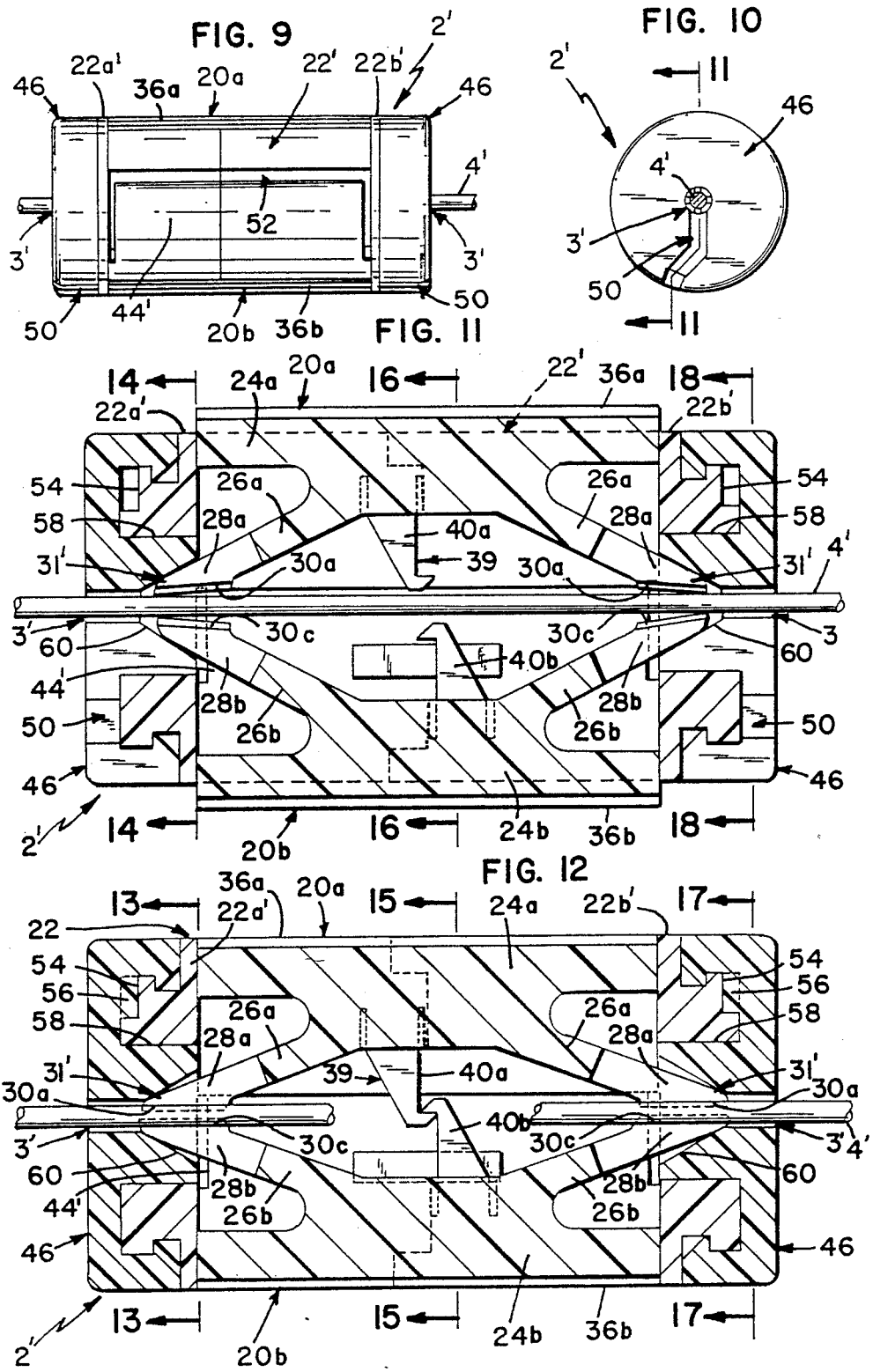

ONE-HANDED PERCUTANEOUS TRANSLUMINAL ANGIOPLASTY STEERING DEVICE AND METHOD

FIELD OF THE INVENTION

The present invention relates to steering or torquing devices for manipulating or guiding a guide wire or catheter for percutaneous transluminal angioplasty and related medical procedures.

BACKGROUND OF THE INVENTION

Percutaneous transluminal angioplasty has recently become well known in the art as a delicate and artful procedure which has revolutionized medical treatment of atherosclerotic stenosis in arteries. The use of a catheter to dilate an atherosclerotic stenosis in blood vessels was first disclosed in 1964 by Dotter and Judkins. These investigators reported the development of a series of coaxial tapered dilating catheters that could be placed percutaneously through femoral artery atherosclerotic obstructions. The technique was subsequently modified by Gruntzig, who developed the balloon catheter concept. Today, balloon angioplasty is widely used to treat arterial stenosis or arterial blockages in lieu of more invasive procedures such as coronary artery bypass grafting, vascular surgery and the like.

Coronary angioplasty is now a very well known procedure. The utility of the present invention will be described in relation to coronary angioplasty although it has applications as a steering device for angioplasty of any vessel, as well as for other medical procedures involving steering a distal end of an elongated wire or strand by manipulating a proximal portion of the strand.

In the initial stages of a coronary angioplasty, a guiding catheter is inserted into the femoral artery in the groin. The guiding catheter is subsequently passed through the femoral artery into the aorta and over the aortic arch, and then maneuvered into the ostium of the coronary artery under fluoroscopic guidance. In order to dilate a coronary artery stenosis, a balloon catheter is directed through the guiding catheter and into the coronary artery until the deflated balloon is positioned across the stenosis. The balloon is then briefly inflated, thereby expanding the stenosis and relieving the blood vessel of the obstruction.

In order to guide the balloon catheter to the location of the stenosis, the balloon catheter is equipped with a guide wire which extends well beyond the distal end of the balloon catheter. The initial step in inserting the balloon catheter into the coronary artery involves advancing the guide wire beyond the guiding catheter and into the coronary artery under fluoroscopic guidance. After the guide wire is in place in the coronary artery, it is used to guide the balloon catheter into position by sliding the balloon catheter along the guide wire. In order to direct the guide wire successfully into position within the coronary artery without causing injury to the lining thereof, precise control of the guide wire is required. To provide such precise control, steering devices have been developed which allow precise rotational control of a J-tip which is generally provided at the distal end of the guide wire. Because the guide wire has extremely limited rotational flexibility, rotation of the steering device will generally result in a corresponding rotation of the J-tip. Because the guide wire must have considerable linear flexibility in spite of the need for limited rotational flexibility, workers in the field note that one may retain good control of the forward movement of the guide wire during insertion into the coronary artery by limiting the distance between the location of the steering device on the guide wire and the hub at the proximal end of the balloon catheter. If the distance between the steering device and the hub of the balloon catheter is relatively large, the control afforded the operator will be diminished because of the increased tendency for the guide wire to bend in a position between the steering device and the hub of the balloon catheter. Therefore, it is important that the distance between the steering device and the hub of the balloon catheter always be minimized. Preferably, this distance will be limited to 2-3 centimeters. Therefore, when the guide wire is being inserted into the coronary artery, the steering device must be repositioned on the guide wire as the guide wire is inserted further and further into the artery. Because this is a very delicate and artful procedure, it is very important for the operator to have as much control of the guide wire as possible. Furthermore, as the operator advances the guide wire, he or she must simultaneously watch a fluoroscopic monitor. Most operators have also found that they must hold the hub of the balloon catheter with one hand as they grasp the steering device with the other hand in order to direct the guide wire. Although the prior art steering devices which are presently available to workers in the field provide for adequate rotational control of the guide wire, it is tedious and distracting to advance the guide wire using these devices because it is necessary to use two hands to reposition them on the guide wire, and the operator's attention is necessarily diverted away from the monitor at a time when the operator needs to be particularly attentive.

The prior art steering devices generally used in the field of angioplasty today comprise a two-piece disposable plastic device having a collet-type gripping mechanism wherein a cap is screwed down over a plurality of flanges which are thereby tightened down upon the guide wire providing a tight grip thereof. Unfortunately, in order to loosen the grip of the steering device, the operator must use two hands. One hand is required to grasp the main body portion of the steering device, while the other hand unscrews the cap portion to loosen the collet-type mechanism. When the steering device is repositioned on the guide wire, both hands are again required to tighten the screw cap so that the manipulation of the guide wire may be continued. It will be appreciated that using both hands to loosen and then tighten the steering device on the guide wire every time the guide wire is advanced 2-3 centimeters can become a very tedious and cumbersome requirement.

The present invention addresses these and other problems associated with the use of a steering device for percutaneous transluminal angioplasty and related medical procedures requiring control of a guide wire or other elongated strand-like tools. The present invention also offers other advantages over the prior art and solves other problems associated therewith.

SUMMARY OF THE INVENTION

Accordingly, it is an object of the present invention to provide an improved guide wire steering device for percutaneous transluminal angioplasty and other related medical procedures which enables operators to fully control the repositioning of the steering device at various positions along a guide wire using one hand. It will be appreciated that because one hand is generally required to grasp the hub of the balloon catheter during manipulation of the guide wire, it would be extremely advantageous to control the gripping mechanism of the steering device with a single hand. Thus, that one would not be required to remove one's hand from the hub of the balloon catheter in order to engage a portion of the steering device so that the device may be repositioned or so that the device may be manipulated to grip the guide wire firmly. Furthermore, one's gaze would not be distracted from the video monitor while repositioning the steering device.

In one embodiment of the present invention, a percutaneous transluminal angioplasty (PTA) steering device for directing passage of a remote portion of a length of wire is provided. The device comprises releasable gripping means for releasably gripping a proximate portion of the length of wire. The gripping means includes opposing gripping faces which cooperate to grip the proximate portion of the length of wire therebetween when the faces are manipulated so that they are in a gripping position. The gripping means further include manipulation means for manipulating the faces into the gripping position. The manipulation means include releasable locking means for locking the gripping faces in the gripping position when opposing portions of said locking means are engaged. The gripping faces occupy a non-gripping position when the opposing portions of said locking means are disengaged. Preferably, said manipulation means includes means for engaging and disengaging said releasable locking means. Said gripping means preferably include opposing gripping members, each opposing gripping member including one of said opposing gripping faces. Preferably, the device further comprises lateral engaging means for engaging the length of wire by slipping the device laterally onto the length of wire.

In another embodiment, the PTA steering device of the present invention comprises opposing gripping members. Each gripping member includes a body member and a gripping flange. Each of the gripping flanges have gripping faces which cooperate to releasably grip a proximate portion of a length of wire when the opposing gripping members are manipulated so that the opposing gripping faces are in a gripping position. The gripping members include releasable locking means for locking said opposing gripping faces in the gripping position when opposing portions of said locking means are engaged. The opposing gripping faces occupy a non-gripping position when the opposing portions of said locking means are disengaged. When the opposing portions of said locking means are disengaged, the length of wire slides freely within said steering device, and when the opposing faces are in the gripping position and said locking means are engaged, the length of wire is substantially bound in an engaged position with respect to the device.

Further features provide additional advantages. These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there are illustrated and described preferred embodiments of the invention.

BRIEF DESCRIPTION OF THE DRAWINGS

In the drawings, in which like reference numerals and letters indicate corresponding parts throughout the several views.

FIG. 3 is a side elevational view of the steering device of FIG. 1;

FIG. 4 is an end view of the steering device shown in FIG. 3;

FIG. 5 is an enlarged cross-sectional view of the steering device as seen from line 5-5 of FIG. 4 showing the device in a non-gripping position;

FIG. 6 is an enlarged cross-sectional view similar to that in FIG. 5 showing the device in a gripping position;

FIG. 7 is a transverse cross-sectional view of the device as seen from the line 7-7 of FIG. 3 showing a locking mechanism in a locked position;

FIG. 8 is a transverse cross-sectional view of the device as seen from the line 8-8 of FIG. 3;

FIG. 9 is a side elevational view of another embodiment of the steering device of the present invention;

FIG. 10 is an end view of the steering device shown in FIG. 9 as seen from left to right;

FIG. 11 is an enlarged cross-sectional view of the steering device as seen from line 11-11 of FIG. 10 showing gripping members in a non-gripping position;

FIG. 12 is an enlarged cross-sectional view similar to the view shown in FIG. 11, but showing the gripping members in a gripping position;

DETAILED DESCRIPTION OF THE PREFERRED EMBODIMENTS

Figure 1:
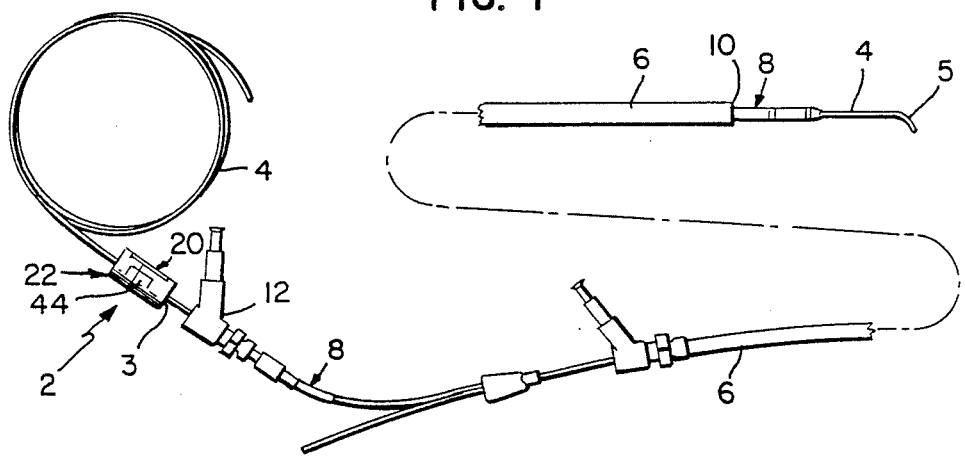
FIG. 1 is a schematic view of a steering device of the present invention in connection to equipment commonly used in percutaneous transluminal angioplasty.
Figure 2:
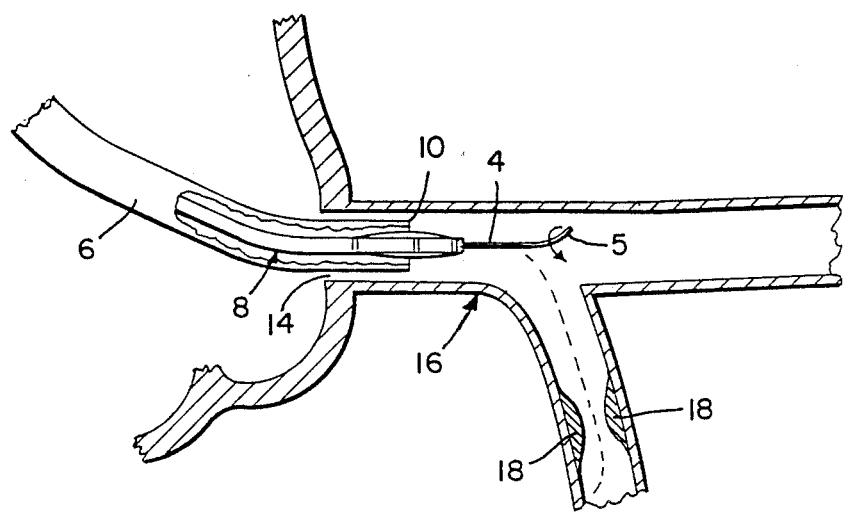
FIG. 2 is a schematic sectional view of a coronary artery with a portion of a guiding catheter and a guide wire and other equipment commonly used in angioplasty, and shown in FIG. 1, inserted therein.
Figure 13:
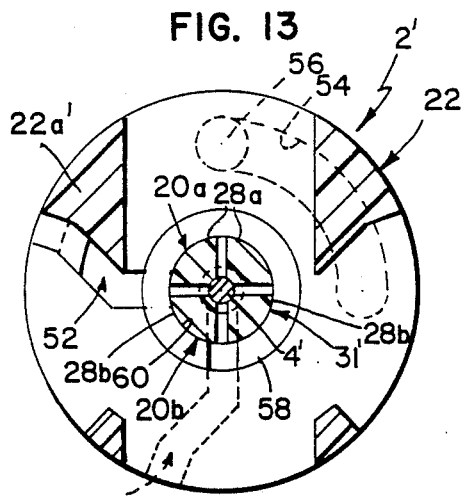
FIGS. 13 and 14 are transverse cross-sectional views as seen from lines 13-13 and 14-14 of FIGS. 11 and 12, respectively.

Referring now to the drawings, and specifically to FIGS. 1 and 2, the steering device 2 of the present invention is used to manipulate or direct a guide wire 4 used in various medical procedures, preferably percutaneous transluminal coronary angioplasty. The steering device 2 grips the guide wire 4, so that the guide wire 4 may be advanced or withdrawn within a guiding catheter 6 which provides a passage for the guide wire 4 and a balloon catheter 8 which may be advanced along the guide wire 4, through the guiding catheter 6 and into the coronary artery 16. A rounded rubberized tip 10 of the guiding catheter 6 is engaged in the ostium 14 of the coronary artery 16 to be sure that the passage provided by the guiding catheter 6 directs the guide wire 4 and, therefore, the balloon catheter 8 into the coronary artery 16 where the balloon catheter 8 may be used to dilate regions of the coronary artery which may be partially obstructed. The steering device 2 is very critical in providing the operator with sufficient control of the guide wire 4 and its tip 5 which is in the shape of a "J". It is believed that the present steering device 2 will provide great advantages over the prior art because it can be manipulated with one hand and does not require a second hand to reposition the device 2 along the guide wire 4. When the guide wire 4 is engaged in a bore 3 (shown in FIGS. 4-7) of the steering device 2 and the steering device 2 grips the guide wire 4, the J-tip 5 can be rotated, as shown by the arrow in FIG. 2, by rotating the steering device 2 along an axis which runs through the center of the bore 3 which is occupied by a proximal portion of the guide wire 4. The J-tip 5 is located at the distal end of the guide wire 4. It is made of extremely flexible material which will bend easily along its axis in a lateral direction, but will not readily twist or provide a high degree of torsional flexibility. The guide wire 4, and its J-tip 5 are designed to allow for lateral flexibility, especially in the J-tip portion 5, while substantially limiting torsional flexibility. In this way, the J-tip 5 of the guide wire 4 may be easily manipulated by rotating the steering device 2 when it is engaged with the guide wire 4 proximate to the J-tip which is inserted into the arterial passageways of the body. With the help of a fluoroscope, the guide wire 4 may be manipulated or directed so that it will extend into areas within the coronary artery 16 which may be partially blocked by a stenosis 18 as is shown in FIG. 2.

Although the present steering device 2 may be used for a wide variety of medical operations involving directing an elongated strand such as the guide wire 4 or other medical tools such as fiber optic cables and the like, it is most preferably used for percutaneous transluminal angioplasty (PTA), especially coronary angioplasty, which is generally carried out in the following manner. The first step is to position the rubberized tip 10 of the guiding catheter 6 in the ostium 14 of the coronary artery. The guiding catheter 6 is a relatively large catheter having a diameter of about 3 millimeters such that the rubberized tip 10 will fit within the ostium 14, but slide no further into the coronary artery 16. The guiding catheter 6 is inserted into the femoral artery near the groin of a patient undergoing angioplasty and is passed from there under fluoroscopic guidance into the aorta, up over the aortic arch, and then maneuvered into the ostium 14 of the coronary artery 16. Once the rubberized tip 10 of the guiding catheter 6 is in place in the ostium 14, its location is confirmed by injecting a small amount of radio-opaque dye so that the dye may be observed fluoroscopically as it passes into the coronary artery 16.

It will be appreciated that fluoroscopic guidance is X-ray guidance. This method of monitoring internal operations within the body employs a low energy radiation which allows workers to see the movement of radio-opaque objects on a video monitor. A radio-opaque dye can be used to visualize the passageway in the coronary artery 16 and to identify a blockage or stenosis 18 in the artery.

It is very important that the guiding catheter 6 is positioned carefully in the ostium 14 of the coronary artery 16 under fluoroscopic guidance. Once it is there, the shape of the guiding catheter 6 is such that it tends to stay in place within the ostium 14 unless it is specifically withdrawn or advanced to another area.

The next step is to insert a guide wire 4 having a very small diameter, preferably about 0.016 to 0.018 inches in diameter, into a passageway created by the guide catheter 6. The guide wire 4 is typically provided with a small J-tip 5 at its distal end. The J-tip 5 is generally made of a very delicate and flexible material, whereas the remainder of the wire 4, although also quite flexible, has virtually no torsional flexibility such that when the guide wire 4 is rotated about its longitudinal axis by an engaged steering device 2 at one position, there is a substantially one-to-one torsional response at the distal end. Once the wire 4 is pushed beyond the tip 10 of the guide catheter 6, it is very easy to monitor by watching the fluoroscope. It is then cautiously maneuvered down the coronary artery 16 past any obstruction or stenosis 18 which may exist therein. Once the wire 4 is in place beyond the obstruction, the very slender balloon catheter 8, which generally has a deflated cross-sectional diameter of about 1.5 mm, is slipped over the wire and through the guiding catheter 6 until it advances coaxially over the wire and into the coronary artery. The balloon catheter 8 has a first lumen which provides a passageway for the guide wire 4, and a second lumen, separate from the first lumen, which connects a compression device to a balloon incorporated in the leading end of the catheter 8 (elements of 8 not shown). The center of the balloon is generally marked by radio-opaque material which can be easily observed on the fluoroscope so that the position of the balloon may be determined. In this way, the balloon may be centered over a lesion in the artery which is to be dilated, and the compression device can then be used to dilate the balloon to accomplish this task.

The balloon catheter 8 is advanced over the guide wire 4 very cautiously. As the balloon catheter 8 is advanced, the guide wire 4 also advances so that each time the balloon catheter 8 is advanced, the guide wire 4 must be withdrawn in a corresponding increment so that the guide wire 4 does not extend too far into the coronary artery 16. This requires that the steering device 2 be manipulated to release the guide wire 4 so that the steering device 2 can be repositioned on the guide wire 4 after the guide wire has been withdrawn an increment corresponding to the increment which the balloon catheter 8 has been advanced. Because the operator is holding a hub 12 of the balloon catheter 8 when the steering device 2 is manipulated, it is extremely advantageous to be able to alternately release and grip the guide wire 4 with the steering device 2 by manipulating the steering device 2 with one hand.

Once the distal end of the balloon catheter 8 is in the desired position, the balloon is inflated with the compression device for a period of typically about 30-60 seconds, during which time the flow of blood through that particular portion of the artery 16 is totally blocked and the plaque in the artery is compressed. The balloon is then deflated and withdrawn back into the guiding catheter 6 leaving the guide wire 4 in the coronary artery 16.

When the prior art steering devices are used, it generally takes two people to properly position the balloon catheter 8 in the coronary artery 16. One person watches the monitor and pulls back on the guide wire 4, and the other person gently pushes the balloon catheter 8 forward. Although the inventive steering device 2 may be used during this operation, it is especially useful for advancing the guide wire 4 into the coronary artery 16 which is an extremely delicate operation and requires great care to avoid injuring the internal lining of the coronary artery 16 with the tip 5 of the guide wire 4. If one wants to maneuver the guide wire 4 past a stenosis, and then through another branch of the artery, one needs to have very good control and a minimum of distraction. If the steering device is locked onto the guide wire 4 in a position which is 6 or 7 cm. back from the hub 12 of the balloon catheter 8 one will have torqueability, but it will be difficult to exert the forward pushing motion on the wire 4 when holding the steering device 2 without flexing the wire in a position between the steering device 2 and the hub 12. It is for this reasons that the steering device 2 must grip the guide wire 4 in a position which is only 2 or 3 or preferably 1 or 2 cm. in back of the hub 12 so that there, will be minimal lateral deflection of the guide wire 4 in positions between the steering device 2 and the hub 12. Therefore, advancing the guide wire 4 into the coronary artery requires a great deal of finesse. It must be advanced very gently. The worker must watch the fluoroscopic monitor to see where the wire 4 is going and hold the steering device 2 in one hand and the hub 12 in the other. It will be appreciated that it would be very distracting and time consuming to look down at the steering device and remove the one hand from the hub 12 in order to use that hand to loosen a screw cap on the forward end of a prior art steering device such as are presently used in the art. In such a situation, the prior art steering device would need to be loosened with two hands, and then moved back 2 or 3, preferably 1 or 2 cm., tightened down again in order to grip the guide wire 4 in a different position. One would then repeat the process of grasping the hub 12, reestablishing visual contact with the monitor, and advancing the guide wire 4 by gently pushing the prior art steering device toward the hub 12 before repeating the repositioning of the prior art steering device again.

If one is not cautious enough when advancing the guide wire 4, the J-tip 5 at the distal end of the guide wire 4 can find its way under the plaque on the inner surface of the artery even if the tip 5 is pushed gently. The plaque can be lifted and may inadvertently cause a serious dissection of the artery which has the potential for severe complications. A great deal of finesse is required as the operator delicately probes his or her way through the narrowing in the arteries. Similarly, when one comes to a branch point in the arteries as the wire is extended further into the vessel, one does not want to make abrupt or gross movements. In addition to pushing under plaque on the inner surface of the vessels, the wire 4 may lift up the thin, delicate inner membrane lining of the vessel called the intima. It is possible that this membrane may be injured and may flop into the lumen of the vessel and obstruct flow.

The present steering device 2 is preferably a disposable device which will preferably be sterilized prior to sale and delivery to an end user. It is designed to move freely up and down an angioplasty guide wire 4 without encountering substantial resistance when it is in a non-gripping position, and it may be locked into a gripping position by using translational force exerted by a single hand.

Referring now to FIGS. 3–8, one embodiment of the steering device 2 of the present invention employs a single gripping member 20 which forces the wire 4 against gripping face 30b of an interior surface 21 of the main body 22 of the steering device 2 proximate the bore 3 when the gripping member 20 is in a gripping position as shown in FIGS. 6–8.

First and second body members 22a and 22b are joined together to form the main body 22. The body members 22a and 22b may be made of any suitable polymeric material that would be selected by one skilled in the art for the present purpose. The two body members 22a and 22b are joined together by suitable means known to those skilled in the art for joining such material together such that the device 2 comprises an integral article of manufacture. The gripping member 20 is preferably made of a somewhat more flexible polymeric material than the material used to make the body member 22. This material, may also be selected from materials which one skilled in the art would find to be suitable for this purpose. The gripping member 20 is preferably integrally molded of a suitable polymeric material and includes a body portion 24 and flange portions 26. The ends of each of the flange portions 26 distal to the body portion 24 are bifurcated into two wedge members 28, each having gripping faces or surfaces 30a which form a part of a gripping mechanism 31 which also includes gripping faces or surfaces 30b on an internal surface 21 of the main body 22 substantially in the geometric center of a transverse cross section of the steering device 2. The gripping member 20 is supported by a leaf spring 32 which, pushes the gripping member 20 away from the guide wire 4, which runs through the bore 3 in the center of the steering device 2. When the gripping member 20 is in a non-gripping position as shown in FIG. 5, the gripping member 20 and the gripping faces 30a are disengaged from the wire 4. When the gripping member 20 is depressed toward the center of the steering device 2, the gripping faces 30a of the gripping member 20 engage the guide wire 4 and press it against the internal surface 21 of the main body 22, especially in the vicinity of the gripping faces 30b of the main body 22, so that the gripping faces 30a and 30b grip the wire 4 and hold it in place. The gripping faces 30b of the main body 22 correspond to, and are located directly opposite to and directly opposed to, the gripping faces 30a of the gripping member 20. The gripping mechanism 31, therefore, includes all of the gripping faces 30a and 30b and also includes recesses 34 in the main body 22 and the walls of the main body 22 which define the recess 34 which force the wedge members 28 against the guide wire 4 when the gripping member 20 is depressed toward the center of the steering device 2. The gripping mechanism also includes the gripping member 20 and the internal surface 21 of the main body 22. When the gripping member 20 is depressed sufficiently, and the gripping faces 30a and 30b grip the guide wire 4, an upper surface 36 of the gripping member 20 will be flush with the rounded outer surface 38 of the steering device 2. Furthermore, the gripping member 20 will depress the leaf spring 32 and a locking mechanism 39 including two latching members 40 will become engaged within the steering device 2 so as to lock the gripping member 20 in a gripping position as shown in FIG. 6–8. When the gripping member 20 is in the gripping position, the locking mechanism 39 is in a locked position. It will be appreciated, however, that the gripping mechanism 31 can be partially actuated to provide some frictional gripping force without actuating the locking mechanism 39, and thereby locking the device 2 in the locked position.

Referring now specifically to FIG. 7, when the gripping member 20 is in the gripping position and the locking mechanism is in the locked position, the latching members 40 are engaged in latch recesses 42 in the main body 22. In order to release the gripping member 20 so that it will be forced away from the center of the steering device 2 by the leaf spring 32 and disengaged from the wire 4, there are release levers 44 on each side of the steering device 2. The release levers 44 form an integral portion of the main body 22. Because the main body 22 is made of a somewhat flexible material, the integral connection between the release levers 44 and the main body 22 acts as a "living hinge" which permit the release levers 44 to be depressed. When they are depressed simultaneously, by exerting translational forces toward the center of the device 2 from both sides, the flexible latching members 40 are forced toward the center of the steering device 2 so that the latching members 40 are pushed out of the latch recesses 42 and the gripping member 20 is released and pushed upward away from the center of the steering device 2, by the resilient leaf spring 32. Therefore, it is possible to depress the gripping member 20 when it is in the non-gripping position shown in FIG. 5, so that it will occupy the gripping position shown in FIG. 6–8, where the locking mechanism 39 is shown in a locked position. In order to release the gripping member 20 from the gripping position shown in FIG. 6–8, the release levers 44 on both sides of the steering device are depressed toward the center of the device 2 to push the latching members 40 away from their corresponding latch recesses 42 so that the locking mechanism 39 will disengage, thereby freeing the gripping member 20 to become disengaged from the guide wire 4 under the biasing force of the leaf spring 32. It will be appreciated that these operations can be accomplished when the steering device 2 is grasped by a single hand and that none of these operations would require the assistance of another hand during maneuvering of the guide wire 4 in the various operations required during an angioplasty procedure.

Figure 14:
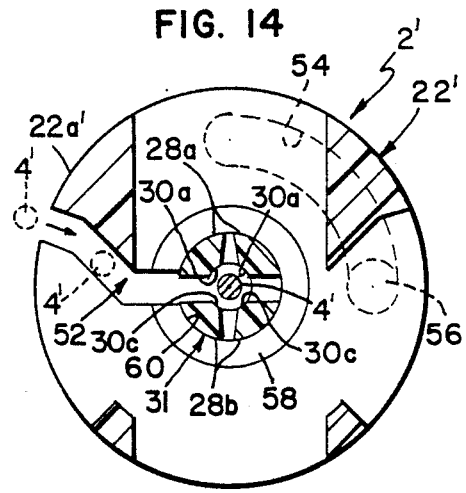
Figure 15:
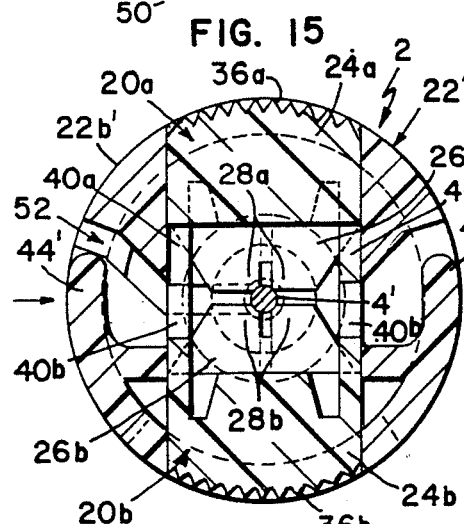
FIGS. 15 and 16 are transverse cross-sectional views as seen from lines 15-15 and 16-16 of FIGS. 11 and 12, respectively.
Figure 16:
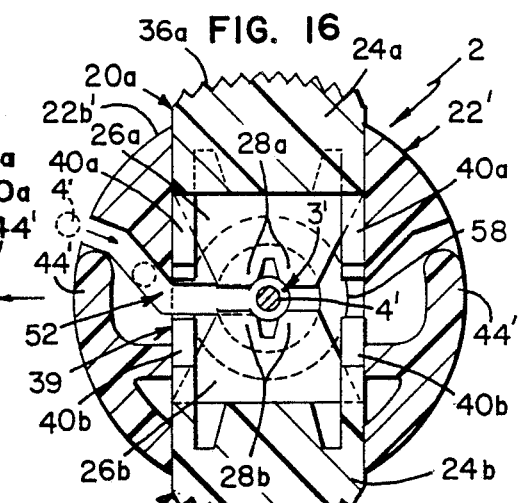
Figure 17:
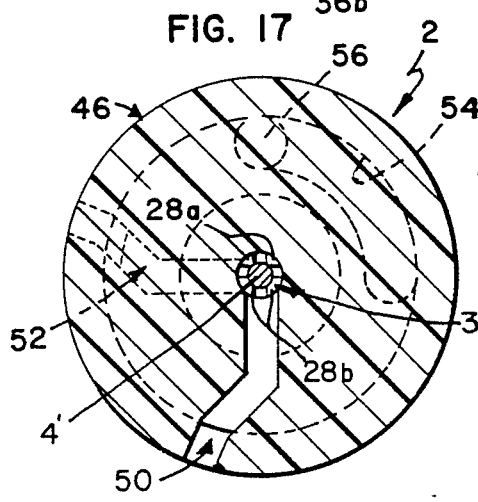
FIGS. 17 and 18 are transverse cross-sectional views as seen from lines 17-17 and 18-18 of FIGS. 11 and 12, respectively.
Figure 18:
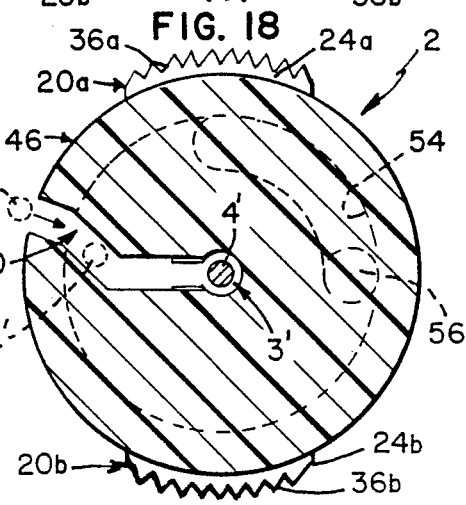

Referring now to FIGS. 9–18, which show a second embodiment 2' of the present invention which includes two opposing gripping members 20a and 20b. The main body 22' of the steering device 2' includes two body members 22a' and 22b' which are joined together in a manner similar to that described for the steering device 2 shown in FIG. 3. Two end caps 46 are rotatably connected to the respective extremities of the main body 22. The end caps 46 may be rotated 90° in order to provide for the alignment of radial channels 50 and 52 in the end caps 46 and the main body 22', respectively. When the respective radial channels 50 and 52 are aligned, as is shown in FIGS. 14, 16 and 18, a length of the guide wire 4' may be inserted transversely into the steering device 2'. In order to prevent the guide wire 4' from coming out of the steering device 2' the end caps 46 can be rotated 90° so that the radial channels 50 and 52 are no longer in alignment. The rotation of the end caps 46 is permitted by indexing recesses 54 in the main body 22' which permits indexing pins 56, which are integral parts of each of the end caps 46, to slide within the respective indexing recesses 54 as the respective end caps 46 are rotated axially with respect to a transverse cross-section of the main body 22'.

When the guide wire 4' is inserted in the steering device 2' as shown in FIG. 11, the gripping members 20a and 20b can be depressed toward the center of the steering device 2' so that the gripping members 20a and 20b engage and grip the guide wire 4'. When the opposing gripping members 20a and 20b are depressed, the respective opposing flange portions 26a and 26b, and particularly the wedge members 28a and 28b, which form the bifurcated end portions of the respective flange portions 26a and 26b, are forced downward and outward toward the respective axial extremities of the steering device 2' and as the respective wedge members 28a and 28b are forced up again bosses 58 in each respective end cap 46 which define conical recesses 60 in the respective end caps 46. When the respective opposing gripping members 20a and 20b are depressed, upper and lower latching members 40a and 40b on each side of the steering device 2' engage so that a locking mechanism 39' is in a locked position. When the locking mechanism 39' is in a locked position, the upper and lower gripping members 20a and 20b are in a gripping position wherein gripping faces 30a of the upper gripping member 20a and 30c of the lower gripping member 20b are engaged with and grip the guide wire 4'. In order to disengage the upper and lower latching members 40a and 40b respectively, which are located on each side of the steering device 2' and, therefore, latch the respective gripping members 20a and 20b on both sides of the guide wire 4', release levers 44' are squeezed to force the lower latching members 40b on each side inward toward bore 3' in the center of the steering device 2'. When the lower latching members 40b are forced inward, they are individually disengaged from the upper latching members 40a, thereby releasing the opposing gripping members 20a and 20b which are then forced away from each other and away from the center of the steering device 2' by the biasing affect of the resilient flange portions 26a and 26b of the respective gripping members 20a and 20b, which are made of a resilient, flexible polymeric material as previously described with respect to the gripping member 20 of the device 2 shown in FIG. 3.

The steering device 2' shown in FIGS. 9–18 is an integral unit and is preferably made of suitable polymeric materials that would be selected by one of skill in the art for such a device. Preferably, these materials include resilient, flexible, polymeric materials which are biocompatible with the intended use. This device 2' is preferably disposable and is preferably sterilized prior to distribution to its end user.

The gripping mechanism 31' of the device 2' includes the opposing gripping members 20a and 20b and their various parts including the opposing gripping faces 30a and 30c. Also included in the gripping mechanism 31' are the bosses 58 in each respective end cap 46 which define the conical recesses 60 in the respective end caps. The bosses 58 wedge the wedge members 28a and 28b against the guide wire 4' when the respective gripping members 20a and 20b are depressed toward the center of the device 2'.

It will be appreciated that the respective gripping mechanisms 31 and 31' and the respective locking mechanisms 39 and 39' which include their respective release levers 44 and 44', may all be actuated using direct translational force exerted by a single hand grasping the respective steering devices 2 and 2'. The translational movement of the respective elements of the respective devices 2 and 2', which results from the translational force applied to these elements is sufficient to actuate respective changes in the various positions occupied by the respective devices 2 and 2'. Translational force, as used herein, means a linear force as opposed to a rotational force.

The present invention enables one of skill in the art to releasably engage a length of wire so as to direct passage of a remote portion of the length of wire during percutaneous transluminal angioplasty and related medical procedures.

As used herein, wire means any elongated strand-like member, such as a PTA guide wire, a fiber optic bundle or strand, a catheter, or the like.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, composition, and arrangement of parts within the principles of the invention to the full extent indicated by the broad general meaning of the terms in which the appended claims are expressed.

What is claimed is:

1. A steering device for directing passage of a remote portion of a length of wire, said steering device comprising releasable gripping means for releasably gripping a proximate portion of the length of wire when said gripping means is manipulated by the exertion of a force upon a gripping member of said gripping means so that the gripping member is moved into a gripping position, said steering device including releasable locking means for locking said gripping member in a gripping position in opposition to an opposing gripping face of said gripping means, said locking means including first and second engaging portions interconnected with said gripping member and said opposing gripping face, respectively, such that when said respective engaging portions are engaged with one another, and the gripping member is in the gripping position, the gripping member is retained in the gripping position by said engaged engaging portions.

2. The steering device of claim 1 wherein said locking means include a release lever which can be actuated when said locking means has been previously actuated to lock said gripping member in a gripping position, wherein the release lever can be actuated by exerting a force upon said release lever wherein said release lever unlocks said gripping member such that said gripping member is no longer in a gripping position.

3. The steering device of claim 2 wherein said device further comprises spring means for biasing said gripping member away from said length of wire such that said gripping members is disengaged from said wire when said release lever is actuated to unlock said gripping member.

4. The steering device of claim 1 wherein said steering device has a single housing structure such that said steering device can be manipulated with one hand, said housing structure including an axial bore and channel means for receiving the length of wire transversely in said axial bore, wherein said length of wire can be inserted transversely into said steering device to occupy a position in the axial bore of said steering device via said channel means.

5. The steering device of claim 4 wherein said housing structure includes a pair of separately rotatable end caps, and wherein said channel means include radial channels in each of said pair of end caps, said housing structure including a main body, said main body including a radial body channel, wherein said length of wire can be inserted transversely into said device via said channel means when said radial channels and said radial body channel are in alignment.

6. A steering device for directing passage of a remote portion of a length of wire, said steering device comprising releasable gripping means for releasably gripping a proximate portion of the length of wire, said gripping means including a gripping member and an opposing gripping face which cooperate to grip the proximate portion of the length of wire when said gripping means is manipulated by the exertion of a force so that said gripping member is in a gripping position, said steering device including integral releasable locking means for locking said gripping member in the gripping position, said locking means including a latch member interconnected with said gripping member and an engaging portion interconnected with said opposing gripping face, said gripping member being retained in a gripping position when said latch member is engaged with said engaging portion.

7. A steering device for directing passage of a remote portion of a length of wire, said steering device comprising releasable gripping means for releasably gripping a proximate portion of the length of wire, said gripping means including opposing gripping surfaces which cooperate to grip the proximate portion of the length of wire when said gripping means is manipulated so that said opposing gripping surfaces are in a gripping position, said steering device further including releasable locking means for locking said gripping surfaces in said gripping position, said locking means being interconnected with said gripping means, wherein said steering device has a single housing structure such that said steering device can be readily manipulated with one hand.

8. The steering device of claim 7 wherein said gripping means include means for engaging and disengaging said releasable locking means.

9. The steering device of claim 8 wherein said gripping means include two opposing gripping members.

10. The steering device of claim 9 wherein each opposing gripping member includes a plurality of gripping surfaces.

11. The steering device of claim 7 further comprising an axial bore and channel means for receiving the length of wire transversely in said axial bore, wherein said length of wire can be inserted transversely into said device to occupy a position in the axial bore of said device via said channel means.

12. A percutaneous transluminal angioplasty (PTA) steering device for directing passage of a remote portion of a length of wire, said steering device comprising releasable gripping means for releasably gripping a proximate portion of the length of wire, said gripping means including opposing gripping faces which cooperate to grip the proximate portion of the length of wire when said gripping faces are manipulated so that they are in a gripping position, said steering device including integral manipulation means interconnected with said gripping means for manipulating said faces into said gripping position, said steering device further including integral releasable locking means interconnected with said gripping means for locking said gripping faces said gripping position, wherein said steering device has a single housing structure such that said steering device can be readily manipulated with one hand.

13. The PTA steering device of claim 12 wherein said locking means include opposing latching members interconnected with respective opposing gripping faces, wherein said latching members can be engaged within said steering device to lock said gripping faces in said gripping position.

14. A method for releasably engaging a length of wire so as to direct passage of a remote portion of the length of wire during percutaneous transluminal angioplasty and related medical procedures, the method comprising the steps of:
  (a) slidably positioning a steering device having a single housing structure onto the length of wire by insertion of the wire into a bore of the housing structure; and
  (b) simultaneously gripping the length of wire with said steering device and locking the steering device in a gripping state by manually applying a first force to an external surface of the steering device, whereby internal gripping faces of the steering device engage the length of wire.

15. The method of claim 14 wherein the steering device is slidably positioned onto the length of wire by engaging the wire laterally and sliding it onto the length of wire.

16. The method of claim 14 further comprising the step of unlocking the steering device by applying a second force to an external surface of the steering device whereby the device is no longer in a gripping state and the length of wire may pass freely through said steering device.

17. The method of claim 14 further comprising the step of releasing the wire by applying a second translational force on an external surface of the steering device whereby gripping faces of the steering device disengage from the length of wire.

18. A percutaneous transluminal angioplasty (PTA) steering device for directing passage of a remote portion of a length of wire, the device comprising opposing gripping members, each gripping member having a main body portion and a gripping flange, each of said gripping flanges having gripping faces, the gripping faces of opposing gripping members cooperating to releasably grip a proximate portion of the length of wire when said opposing gripping members are manipulated so that said opposing gripping faces are in a gripping position, said gripping members including releasable locking means for locking said opposing gripping faces in said gripping position when opposing portions of said locking means are engaged, said opposing gripping faces being in a non-gripping position when said opposing portions of said locking means are disengaged, the length of wire sliding freely within said steering device when said opposing portions of said locking means are disengaged and the length of wire being substantially bound in an engaged position with respect to said device when said opposing faces are in said gripping position and said locking means are engaged.

19. A method for releasably engaging a length of wire so as to direct passage of a remote portion of the length of wire during percutaneous transluminal angioplasty and related medical procedures, the method comprising the steps of:
  (a) slidably positioning a steering device including releasable gripping means for releasably gripping a approximate portion of the length of wire onto the length of wire by insertion of the wire into the device, said gripping means including opposing gripping surfaces which cooperate to grip the proximate portion of the length of wire therebetween when said gripping means is manipulated by the exertion of a translational force upon said gripping means so that gripping surfaces are moved into a gripping position; and
  (b) simultaneously gripping the length of wire with said steering device and locking the steering device in a gripping state by applying a translational force to said gripping means, whereby gripping surfaces engage the length of wire.

20. The method of claim 19 wherein said steering device includes an axial bore and channel means for receiving the length of wire transversely in said axial bore, said step of slidably positioning said steering device onto the length of wire including inserting said length of wire into said channel means.

21. The method of claim 19 further comprising the step of unlocking the steering device by applying a second force to an external surface of the steering device whereby the device is no longer in a gripping state and the length of wire may pass freely through said steering device.

22. The steering device of claim 10 wherein each opposing gripping member includes four gripping surfaces.

* * * * *

UNITED STATES PATENT AND TRADEMARK OFFICE
CERTIFICATE OF CORRECTION

PATENT NO. : 4,957,117
DATED : 9/18/90
INVENTOR(S) : Douglas G. Wysham

It is certified that error appears in the above-identified patent and that said Letters Patent is hereby corrected as shown below:

In the Abstract, line 6, delete "and" after the word "includes"

In column 7, line 10 delete "," after the word "there"

In column 8, line 21 delete "," after the word "which"

In column 11, line 44 "members" should read --member--

In column 14, line 14, "approximate" should read --a proximate--

Signed and Sealed this

Seventeenth Day of March, 1992

Attest:

HARRY F. MANBECK, JR.

*Attesting Officer*    *Commissioner of Patents and Trademarks*